(12) United States Patent
Presura et al.

(10) Patent No.: US 9,980,655 B2
(45) Date of Patent: May 29, 2018

(54) HEART RATE MONITOR DEVICE

(71) Applicant: KONINKLIJKE PHILIPS N.V., Eindhoven (NL)

(72) Inventors: Cristian Nicolae Presura, Veldhoven (NL); David Antoine Christian Marie Roovers, Eindhoven (NL); Ruxandra Valentina Bobiti, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 73 days.

(21) Appl. No.: 15/110,625

(22) PCT Filed: Mar. 9, 2015

(86) PCT No.: PCT/EP2015/054802
§ 371 (c)(1),
(2) Date: Jul. 8, 2016

(87) PCT Pub. No.: WO2015/139980
PCT Pub. Date: Sep. 24, 2015

(65) Prior Publication Data
US 2017/0258338 A1 Sep. 14, 2017

(30) Foreign Application Priority Data

Mar. 17, 2014 (EP) .................................... 14160183

(51) Int. Cl.
*A61B 5/0205* (2006.01)
*A61B 5/11* (2006.01)
(Continued)

(52) U.S. Cl.
CPC ............ *A61B 5/02055* (2013.01); *A61B 5/11* (2013.01); *A61B 5/6815* (2013.01);
(Continued)

(58) Field of Classification Search
CPC ............ A61B 5/02055; A61B 5/02416; A61B 5/02438; A61B 5/08; A61B 5/11;
(Continued)

(56) References Cited

U.S. PATENT DOCUMENTS 5,746,697 A  5/1998  Swedlow et al.
2007/0244398 A1* 10/2007 Lo ...................... A61B 5/02444
                                                600/500
(Continued)

FOREIGN PATENT DOCUMENTS

EP     2116183 A1   11/2009
EP     2457505 A1    5/2012
WO  2010133996 A1   11/2010

*Primary Examiner* — Michael Carey

(57) ABSTRACT

A heart rate monitor system (100) for monitoring a heart rate of a user is provided. The heart rate monitor system (100) comprises at least one primary heart rate sensor (110) for measuring or determining a heart rate of a user. The at least one primary heart rate sensor (110) has a first power consumption. The heart rate monitor system (100) also comprises at least one secondary sensor (120) for measuring at least one physiological factor influencing the heart rate of a user. The at least one secondary sensor (120) has a second power consumption which is lower than the first power consumption of the at least one primary heart rate sensor (110). The heart rate monitor system (100) further comprises a power management unit (160) for managing an operation and/or power consumption of the at least one primary heart rate sensor (110) based on information (126) from the at least one secondary sensor (120). The heart rate monitor system comprises a model unit for estimating a heart rate of a user based on a model stored in the model unit and information received from the at least one secondary sensor. The model unit is coupled to the power management unit via a feedback loop such that the power management unit is adapted to compare the estimated heart rate with the mea- (Continued)

sured heart rate and to control the operation of the primary sensor in dependence on the comparison.

7 Claims, 1 Drawing Sheet

(51) Int. Cl.
*A61B 5/00* (2006.01)
*A61B 5/08* (2006.01)
*A61B 5/024* (2006.01)

(52) U.S. Cl.
CPC .......... *A61B 5/6824* (2013.01); *A61B 5/7278* (2013.01); *A61B 5/02416* (2013.01); *A61B 5/02438* (2013.01); *A61B 5/08* (2013.01); *A61B 2560/0209* (2013.01); *A61B 2562/029* (2013.01); *A61B 2562/0219* (2013.01)

(58) Field of Classification Search
CPC ... A61B 5/6815; A61B 5/6824; A61B 5/7278; A61B 2560/0209; A61B 2560/0219; A61B 2560/029
USPC .................................................. 600/300, 301
See application file for complete search history.

(56) References Cited

U.S. PATENT DOCUMENTS

| | | |
|---|---|---|
| 2008/0058616 A1 | 3/2008 | Nakagawa et al. |
| 2012/0130201 A1* | 5/2012 | Jain .......................... A61B 5/08 600/301 |
| 2012/0203077 A1 | 8/2012 | He et al. |
| 2012/0215115 A1 | 8/2012 | Takahashi |
| 2013/0217978 A1 | 8/2013 | Ma |
| 2014/0073486 A1* | 3/2014 | Ahmed .............. A61B 5/02405 482/9 |

\* cited by examiner

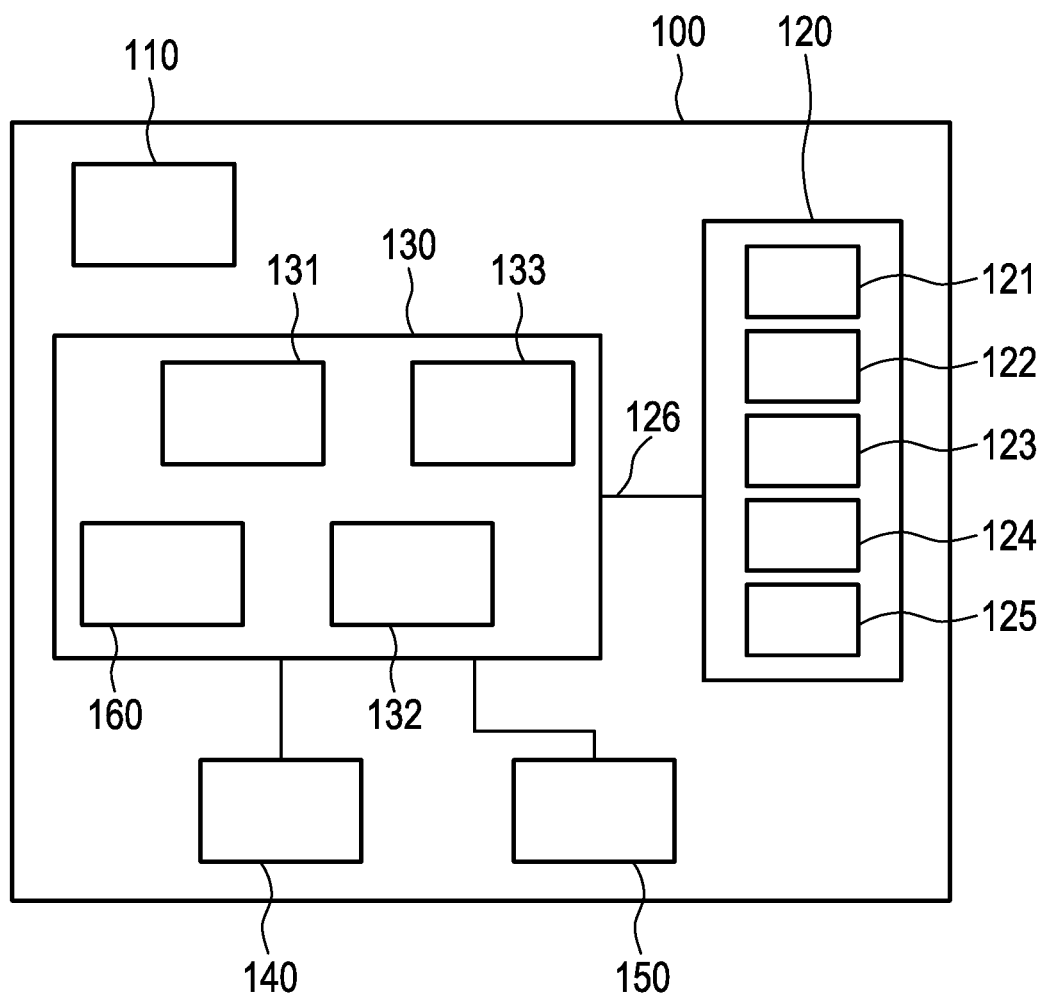

HEART RATE MONITOR DEVICE

CROSS-REFERENCE TO PRIOR APPLICATIONS

This application is the U.S. National Phase application under 35 U.S.C. § 371 of International Application No. PCT/EP2015/054802, filed on Mar. 9, 2015, which claims the benefit of European Patent Application No. 14160183.1 filed on Mar. 17, 2014. These applications are hereby incorporated by reference herein, for all purposes.

FIELD OF THE INVENTION

The invention relates to a heart rate monitor device for monitoring a heart rate of a user, a method for monitoring a heart rate of a user and a computer program for monitoring a heart rate of a user.

BACKGROUND OF THE INVENTION

The monitoring of a heart rate of a user for example by means of optical sensors is well known. Here, an optical sensor emits light into the skin of a user. The emitted light is scattered within the skin and reflected light exits the skin and is captured by an appropriate sensor. Based on the received signals from the sensor, the heart rate of a user can be determined.

US 2007/0244398 A1 discloses a heart rate monitor which uses ultrasound, infrared, pressure sensing, radio frequency or laser technology to measure a heart rate. Furthermore, this heart rate monitor also implements a power saving algorithm. This is performed by reducing or switching off the power of the sensors between expected heart beats.

US 2014/0073486 A1 discloses a lightweight wearable system adapted to collect various physiological data continuously from a user. The system comprises a heart rate monitor for monitoring the heart rate of the user. The system comprises a processing module that may receive data on the motion of the user using, for example, from an accelerometer. The processing module may process the motion data to determine a motion status of the user and, based on the motion status, may adjust the duty cycle of the heart rate monitor.

EP2457505A1 discloses a sensor array comprising one or more sensors. A sensor receives a stimulus and converts it into a data stream. Sensors may include sensors that are carried by the user such as a heart-rate monitor. One or more sensors in the sensor array may have a dynamic sampling rate. For example, if the stimulus measured by a sensor is different from the outcome predicted by some model or falls outside some threshold range, the sensor may increase or decrease its sampling rate in response.

SUMMARY OF THE INVENTION

It is an object of the present invention to provide a heart rate monitor device and system, a corresponding method and a computer program for monitoring a heart rate of a user with an improved power saving capability.

In an aspect of the present invention, a heart rate monitor device for monitoring a heart rate of a user is provided. The heart rate monitor device comprises at least one primary sensor for measuring or determining a heart rate of a user. The at least one primary sensor has a first power consumption. The heart rate monitor device furthermore comprises a power management unit for managing an operation and/or power consumption of the at least one primary sensor, based on measurements or information from at least one secondary sensor which is measuring at least one physiological factor influencing the heart rate of the user. The at least one secondary sensor has a second power consumption which is lower than the power consumption of the at least one primary sensor. The heart rate monitor device comprises a model unit for estimating or predicting a heart rate of a user based on a model stored in the model unit and information received from the at least one secondary sensor. The model unit is coupled to the power management unit via a feedback loop such that the power management unit is adapted to decrease the sampling frequency and/or measurement intensity of the primary sensor if the estimated heart rate and the measured heart rate correspond to each other.

By using the at least one secondary sensor with a reduced power consumption to measure or detect at least one physiological factor that is influencing the heart rate, the operation and/or power consumption of the at least one first sensor can be controlled. The power consumption of the at least one first sensor can be reduced by on and off switching of the at least one sensor, by decreasing the sample frequency of the user and/or by decreasing the output intensity of the sensor. The information or measurements from the secondary sensor are used as input for the power management unit. In other words, the operation and/or power consumption of the primary sensors is controlled based on the output of the secondary sensors. Based on the model stored in the model unit and measurements from the secondary sensor, a heart rate of a user can be predicted. Having the predicted heart rate as given by the model unit, the power management unit can decide in a reliable manner whether or not to influence the operation of the primary sensor in order to reduce its power consumption. If the heart rate of a user can be predicted with a reasonable certainty, this could lead to a situation where the power management unit can control the primary sensor to reduce its power consumption. For example, if the physiological factors are stable, then the heart rate can be estimated with good accuracy and the information from the primary sensor sensing the heart rate is not required such that the power consumption of the primary sensor can be reduced.

Accordingly, in order to save power, the primary heart rate sensor can be switched off, its sampling frequency can be reduced or the measurement intensity can be reduced. This is all performed based on information from the secondary sensors.

According to a further aspect of the invention, the physical factors influencing the heart rate measured by the secondary sensors are breath of the user, speed of the user, acceleration of the user, humidity on the skin of the user, altitude of the user and/or temperature of the user. These physiological factors are known to have an influence on the heart rate of a user. Therefore, these factors are measured, a prediction or estimation on the heart rate of a user can be made and thus, in specific cases, the operation of the primary heart rate sensor can be adapted in particular to reduce the power consumption.

In an aspect of the invention, the at least one secondary sensor can be an internal or an external sensor with respect to the heart rate monitor device. In other words, the primary and secondary sensors can be arranged in a single housing or the at least one second sensor can be arranged outside the housing of the at least one first sensor. Accordingly, the at least one secondary sensor can be arranged adjacent to the first sensor or at another position.

According to an aspect of the invention, a method of monitoring a heart rate of a user is provided. The method comprising a step of measuring a heart rate of a user by at least one primary sensor, wherein the at least one primary sensor has a first power consumption, and a step of managing the operation and/or power consumption of the at least one primary sensor based on information received from at least one secondary sensor measuring at least one physiological factor influencing the heart rate of the user, wherein the at least one secondary sensor has a second power consumption which is lower than the first power consumption. The method further comprises a step of estimating a heart rate of the user based on a model stored in a model unit and the information received from the at least one secondary sensor, and a step of comparing the estimated heart rate with the measured heart rate so as to decrease the sampling frequency and/or measurement intensity of the primary sensor (110) if the estimated heart rate and the measured heart rate correspond to each other.

These and other aspects of the invention will be apparent from and elucidated with reference to the embodiment(s) described hereinafter.

BRIEF DESCRIPTION OF THE DRAWINGS

In the following drawings:

FIG. 1 shows a schematic block diagram of a heart rate monitor system according to the invention.

DETAILED DESCRIPTION OF EMBODIMENTS

The heart rate monitor system according to the invention is based on the following principle. A primary sensor, for example an optical sensor, is used to measure the heart rate of a user. A secondary low power sensor is used to measure or determine physiological factors that are influencing the heart rate of a user. The information from the secondary sensors is used to control the operation and power consumption of the primary sensor. If based on the information from the secondary sensor a control unit determines for example that the heart rate is stable, then for example the sampling rate of the primary sensor can be decreased. If the secondary sensors detect that for example, due to a movement, the heart rate of the user will increase, then for example the sample rate of the primary sensor can be increased again.

FIG. 1 shows a schematic block diagram of a heart rate monitor system according to the invention. The heart rate monitor system 100 comprises at least one primary sensor 110 for measuring or determining a heart rate of a user, at least one secondary sensor 120 for measuring or determining at least one physiological factor influencing the heart rate of a user. The heart rate monitor system 100 furthermore comprises optionally a control unit 131 for controlling the operation of the at least one primary sensor 110. Optionally, a processing unit 132 is provided for processing the output of the at least one primary sensor 110 to determine the heart rate of a user. Optionally, the heart rate monitor system can comprise a display 140 for displaying the heart rate and/or an output 150 for outputting the measured or determined heart rate.

According to an aspect of the invention, the heart rate monitor system 100 can be arranged at a wrist or a forearm or behind an ear of a user.

The primary sensor 110 can be implemented as on optical sensor which comprises a light source for example in form of an LED for producing artificial light. The light source emits the artificial light onto the skin of a user. Within the skin, the emitted artificial light is partially absorbed by the blood within the blood vessels and the artificial light can be scattered throughout the skin and can be reflected back to a photo detector which may also be part of the optical sensor 110. The photo detector is detecting the reflected light through the skin of the user and is generating an output signal.

The output signal of the optical sensor 110 can be forwarded to the processing unit 132. Optionally, the processing unit 132 can also be arranged in the optical sensor 110. The processing unit 132 receives the signal from the optical sensor 110 and determines a pulse rate or a heart rate of the user based on the output signal of the primary sensor 110.

The heart rate monitor system 100 furthermore comprises a power management unit 160. The power management unit 160 serves to control a power consumption and/or operation of the heart rate monitor system and in particular the power consumption of the primary sensor 110. The power management unit 160 can be implemented as a dedicated unit. In addition or alternatively, the function of the power management unit 160 can be performed by the control unit 131 or the processing unit 132. In addition, the control unit 131, the processing unit 132 and the power management unit 160 can be implemented by a μ controller 130. Furthermore, the heart rate monitor system comprises a model unit 133 which can optionally also be implemented by the μ controller 130.

The power management according to an aspect of the invention uses information 126 from secondary sensors to control the power consumption of the primary sensor or the entire heart rate monitor system. In particular, the addition information from the secondary sensors can be used to control the activation and deactivation (on/off switching) of the primary sensor, the sample rate and/or the measuring intensity of the primary sensor 110. In other words, the power consumption of the primary sensor 110 or the overall system can be reduced.

It is well known that the heart rate of a person is dependent on several factors like the physical condition of the user, the motion rate, the activity of the user, the emotional condition of the user as well as internal and external factors. By means of the secondary sensors, information can be gathered which relate to factors which have an influence on the heart rate. The physiological factors that can be measured by the secondary sensors are breath, speed of the user, acceleration of the user, humidity on the skin of the user, altitude, etc.

Based on the information 126 of the physical factors as determined by the secondary sensors 120, the operation and/or power consumption of the primary sensor 110 can be controlled by the power management unit 160. This can be performed if the information from the secondary sensors is sufficient to estimate or predict the heart rate of the user. If the prediction or estimation is good enough, for example the sampling rate of the primary sensor can be reduced. In addition or alternatively, the primary sensor 110 can be activated and deactivated at least for a duration during which the heart rate can be estimated accurately enough. However, if changes in the heart rate appear which can be detected by the outputs of the secondary sensors (e.g. as the motion pattern changes), the operation of the primary sensor can be activated again to determine the exact heart rate.

In other words, during time periods where the heart rate is constant or substantially constant, the sampling frequency of the primary sensor can be reduced. Alternatively, during such periods of time, the primary sensor can be deactivated in order to save power.

According to an aspect of the invention, the activation and deactivation (on/off switching of the primary sensor) can be controlled by the power management unit 160. If by one of the secondary sensors, for example the accelerometer 124, it can be determined that the user is in a constant motion or is not moving, then it can be determined that the heart rate of the user will also not change significantly. As soon as the secondary sensors 120 detect a change in the motion or motion pattern of the user, the primary heart rate sensor 100 can be activated again to measure the actual heart of the user.

According to an aspect of the invention, the primary heart rate sensor 110 can be controlled to measure the heart rate at specific time intervals, wherein the time intervals can vary depending on the change of the motion of the user. If the primary user is activated intermittently instead of continuously, the power consumption can be reduced.

According to an aspect of the invention, the secondary sensors can be a humidity sensor 121, an altimeter 122, a GPS sensor 123, an accelerometer 124 and/or a pressure sensor 125. The humidity sensor 121 can be used to measure the humidity on the skin of a user. The humidity on the skin of the user can be a parameter indicating emotions, physiological conditions of the user and changes in the mood. The altimeter 122 can for example be used to determine the altitude of the user. This may give an indication whether the user is gliding, climbing, etc. The GPS sensor 123 can be used as a speed sensor for example thus determining whether the user is cycling, racing, etc.

The pressure sensor 125 can be used as an air pressure meter. The information from this sensor can be used as an altimeter, or a weather station. When the air pressure is high, there may be persons that react to it with an elevated heart rate.

According to an aspect of the invention, the heart rate monitor system comprises a model unit 133. The outputs of the secondary sensors 120 are received by the model unit 133 and based on a model which is stored in the model unit 133, a heart rate is predicted or estimated based on the information 126 from the secondary sensors 120. The model unit is connected to the power management unit via a feedback loop and the predicted heart rate is then used by the power management unit 160 to control the operation and/or power consumption of the primary sensor.

The operation of the primary heart rate sensor can be controlled by the power management unit 160 by controlling the sampling rate and the intensity of the measurement. If the primary sensor 110 is for example implemented as an optical sensor, the sampling rate and the light intensity of the optical sensors can be controlled. For example based on the predicted heart rate which is output of the model unit 130, the power management unit 160 can decrease the sampling rate or decrease the intensity of the light sources of the optical sensor.

According to the invention, the power management unit 160 can compare the predicted heart rate of the model unit 133 with the heart rate as measured by the primary sensor 110. If the difference between the measured and the predicted heart rate is low (i.e. the predicted and the measured heart rate correspond to each other), then the sampling rate or the measurement intensity can be reduced. However, if the difference between the measured and predicted heart rate is high, the sampling frequency can be increased and/or the measurement intensity (light intensity) can be increased.

According to the invention, the heart rate monitor system 100 can have a housing which accommodates the primary sensor 110 as well as the at least one secondary sensor 120. However, alternatively, the secondary sensors 120 can be arranged outside of a housing of the primary sensor 110. For example, some of the secondary sensors may be part of an external device like a smartphone etc. The secondary sensors 120 may also be arranged at other parts of the body as the housing of the primary sensor 110.

According to the invention, the secondary sensor 120 is a motion sensor such as an accelerometer. The model unit 133 is thus able to predict the heart rate of the user based on a model stored in the model unit taking into account current and past measurements received from the motion sensor. For example, a heart rate at rest is predicted when low motion is measured and a heart rate higher than the heart rate at rest is predicted in case of higher level of motion measured by the motion sensor. The predicted heart rate is derived from models which are stored in the model unit 133. The models give the evolution of heart rate as a function of motion taking into account for example parameters such as the temperature, the altitude, the age of the user, etc.

The heart rate monitor system can be arranged as a wrist device. The heart rate monitor system can also be arranged as a device worn at or on an ear of the user. The monitoring device may also be part of glasses worn by the user. The heart rate monitor device may also be part of a hearing aid or can be worn by the user.

The primary sensor 110 can be embodied as an optical sensor, an electrical sensor and/or a pressure sensor. The secondary sensors can be embodied as a humidity sensor, a speed sensor, an acceleration sensor, an altimeter, etc. The secondary sensors have a power consumption that is lower than the power consumption of the primary sensor.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the measurement of a heart rate or physiological factor influencing the heart rate of the user, the management of the operation and/or power consumption of the primary sensor performed by one or several units or devices can be performed by any other number of units or devices. These procedures and the control of the heart rate monitor system in accordance with the method of monitoring a heart rate of a user can be implemented as program code means of a computer program and/or as dedicated hardware.

A computer program may be stored and/or distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. Heart rate monitor device for monitoring a heart rate of a user, comprising:
    at least one primary sensor for measuring a heart rate of user, wherein the at least one primary sensor has a first power consumption,
    at least one secondary sensor for measuring at least one physiological factor influencing the heart rate of a user, wherein the at least one secondary sensor has a second power consumption which is lower than the first power consumption, a power management unit for managing an operation of the at least one primary sensor based on information received from the at least one secondary sensor, a model unit for estimating the heart rate of a user based on a model stored in the model unit and the information received from the at least one secondary sensor, wherein the model unit is coupled to the power management unit via a feedback loop such that the power management unit is adapted to decrease a sampling frequency and/or measurement intensity of the primary sensor if the estimated heart rate and the measured heart rate correspond to each other.

2. Heart rate monitor device according to claim 1, wherein the at least one physiological factor influencing the heart rate measured by the at least one secondary sensor is at least one of breath of the user, speed of the user, acceleration of the user, humidity on the skin of the user, altitude of the user and/or temperature of the user.

3. Heart rate monitor device according to claim 1, wherein the at least one primary sensor is an optical sensor.

4. Heart rate monitor device according to claim 1, wherein the at least one secondary sensor is a motion sensor, for example an accelerometer.

5. Heart rate monitor device according to claim 1, which is arranged as a wrist device.

6. Method of monitoring a heart rate of a user comprising the steps of:

measuring a heart rate of a user by at least one primary sensor, wherein the at least one primary sensor has a first power consumption, measuring at least one physiological factor influencing the heart rate of the user by at least one secondary sensor, wherein the at least one secondary sensor has a second power consumption which is lower than the first power consumption, managing the operation and/or power consumption of the at least one primary sensor based on information received from the at least one secondary sensor, estimating a heart rate of the user based on a model stored in a model unit and the information received from the at least one secondary sensor, and comparing the estimated heart rate with the measured heart rate so as to decrease a sampling frequency and/or measurement intensity of the primary sensor if the estimated heart rate and the measured heart rate correspond to each other.

7. A non-transitory computer readable medium for monitoring a heart rate of a user in a heart rate monitor device as defined in claim 1, the non-transitory computer readable medium comprising a program code for causing the heart rate monitor device to carry out the steps of the method of monitoring a heart rate of a user as defined in claim 6 when the program code is run on a processor controlling the heart rate monitor system.

* * * * *